(12) United States Patent
Anapliotis et al.

(10) Patent No.: US 8,177,820 B2
(45) Date of Patent: May 15, 2012

(54) BONE PLATE COMPRISING AT LEAST ONE SCREW TO BE FIXED AT A STABLE ANGLE

(75) Inventors: Emmanuel Anapliotis, Berlin (DE); Curt Kranz, Berlin (DE)

(73) Assignee: Merete Medical GmbH (DE)

(*) Notice: Subject to any disclaimer, the term of this patent is extended or adjusted under 35 U.S.C. 154(b) by 637 days.

(21) Appl. No.: 12/095,838

(22) PCT Filed: Aug. 30, 2006

(86) PCT No.: PCT/DE2006/001508
§ 371 (c)(1),
(2), (4) Date: May 26, 2009

(87) PCT Pub. No.: WO2007/025520
PCT Pub. Date: Mar. 8, 2007

(65) Prior Publication Data
US 2009/0306723 A1    Dec. 10, 2009

(30) Foreign Application Priority Data
Sep. 1, 2005    (DE) .................... 20 2005 013 868 U

(51) Int. Cl.
*A61B 17/80*    (2006.01)
(52) U.S. Cl. ............................. 606/283; 606/61; 606/69
(58) Field of Classification Search .................. 606/291, 606/283–285, 289, 290, 294, 910, 280
See application file for complete search history.

(56) References Cited

U.S. PATENT DOCUMENTS
3,741,205 A    6/1973    Markolf et al.
(Continued)

FOREIGN PATENT DOCUMENTS
FR    2 667 913 A1    4/1992
FR    2 739 151 A1    3/1997
WO    97/09000 A1    3/1997

OTHER PUBLICATIONS

International Search Report for parent application PCT/DE2006/001508, having a mailing date of Feb. 8, 2007.
(Continued)

*Primary Examiner* — Thomas C. Barrett
*Assistant Examiner* — Samuel Hanna
(74) *Attorney, Agent, or Firm* — Andrus, Sceales, Starke & Sawall, LLP

(57) ABSTRACT

Disclosed is a bone plate comprising at least one screw that is to be fixed at a stable angle to at least one through-hole and at least one bone screw which is provided with an external thread in the top region. Said external thread tapers more in the screwing direction than a mating thread of the through-hole embodied as an internal thread such that the top of the bone screw is clamped in a stable direction in a torsion-proof manner when the bone screw is screwed in. The bone plate is configured elastically in at least one area adjoining the through-hole such that the material of the bone plate is not deformed in the ductile area because of the expansion resulting from the head of the bone screw being screwed in. As a consequence, the area surrounding the through-hole is not overstretched in any position of the bone screw along the entire length of the threads because of the interaction between the external thread of the top of the bone screw and the internal thread of the plate while the torsion-proof condition is maintained.

15 Claims, 3 Drawing Sheets

U.S. PATENT DOCUMENTS

| | | | |
|---|---|---|---|
| 6,306,140 B1 | 10/2001 | Siddiqui | |
| 6,730,091 B1 * | 5/2004 | Pfefferle et al. | 606/70 |
| 2002/0045897 A1 * | 4/2002 | Dixon et al. | 606/61 |
| 2003/0078668 A1 * | 4/2003 | Michelson | 623/17.16 |
| 2004/0073218 A1 | 4/2004 | Dahners | |
| 2005/0015092 A1 * | 1/2005 | Rathbun et al. | 606/96 |
| 2005/0165400 A1 * | 7/2005 | Fernandez | 606/69 |
| 2005/0192577 A1 * | 9/2005 | Mosca et al. | 606/69 |

OTHER PUBLICATIONS

"Orthopaedic Product News", Aug. 2005, Retrieved from the Internet: URL:http://www.orthoworld.com/us_opn-2005-08.pdf [retrieved on May 26, 2009], p. 30, Hallux Valgus Correction with a Low Profile Locking Plate.

* cited by examiner

BONE PLATE COMPRISING AT LEAST ONE SCREW TO BE FIXED AT A STABLE ANGLE

CROSS-REFERENCE TO RELATED APPLICATIONS

This application is the U.S. national stage application of International Application No. PCT/DE2006/001508, filed Aug. 30, 2006, which International application was published on Mar. 8, 2007, as International Publication No. WO 2007/025520 A1 in the German language, which application is incorporated herein by reference. The International application claims priority of German Patent Application No. 20 2005 013 868.1, filed Sep. 1, 2005, which application is incorporated herein by reference.

FIELD

The present disclosure relates to a bone plate with at least one screw for angularly stable fixation.

BACKGROUND

Such a bone plate is known as the "Metafix," an implant from Merete Medical GmbH, Berlin. It is used for fixing of the so-called hallux-valgus deformity. It is important here that the toe areas to be fixed are held in a directionally stable manner by the plate. To this end the screws comprise not only a bone screw thread for fixing in the bones in their lower region, but also the head area is provided with an external fine thread that engages into a corresponding internal thread of the screw hole of the plate when the screw has reached the corresponding position when being screwed in. This then aligns it in a directionally stable manner. In order to also fix it in the direction of screwing it is subsequently tightened, as is customary for a screw with a head, during which the conical external thread of the head is fixed in the cylindrical internal thread of the plate.

This has the disadvantage that the region of the fixing of the thread, and therewith the end position of the screw, is precisely determined, so that the adjustment region of the screw, and also that of the plate, is limited. A corresponding implant is also known from U.S. Pat. No. 3,741,205; however, in it smooth pins are used instead of screws, so that the conditions are simplified as regards the screwing-in procedure.

Furthermore, an orthopedic plate system is known from published US Patent Application No. 2004/0073218A1 in which an orthopedic screw with a head comprising a thread should be able to be screwed in in different directions. However, no corresponding counterthread is present in the plate for the head so that it finds no firm hold in it. Moreover, the thread of the screw head becomes scored in the plate, producing material chips, so that the consequence is an endangering of the patient.

A bone screw known from U.S. Pat. No. 6,306,140B1 also comprises a head provided with a thread. However, this screw is not intended to be used with bone plates.

SUMMARY

The present inventors have recognized the basic problem of further developing a bone plate of the initially mentioned type in such a manner that the adjustment range of the screw is enlarged so that a fixing of the screw does not occur abruptly but rather its tight fix is given in a larger range. As a consequence, the screw can be further tightened and the seat and the compression of the plate are improved without the screw being overturned or stripped.

The advantages of the bone plate in accordance with the present disclosure particularly reside in the fact that the region following the external thread of the plate is elastically deformed in such a manner that it adapts to the external diameter of the cone of the internal thread, and indeed over the entire path of the screw passage. The fixation screw can therefore be completely "screwed through" the hole in the plate, during which the head is held by the elastic tension in every position in a rotationally secure manner on the one hand and, on the other hand however, the plate is also not irreversibly deformed, that is, overextended, in its plastic area. It can be achieved in this manner that the screw can be sensitively screwed in precisely as far as is necessary to fix the plate firmly applied to the bone, and at the same time it can be ensured that the screw head also does not project above the plate in its highest ranges, so that the fixed plate on the whole, with its screws, forms a unit that essentially closely and smoothly rests on the bone without substantial elevations.

The dimensions of the webs surrounding the screw holes are selected in such a manner that the expansion necessary for the passage of the screw head, that corresponds to the active circumferential difference of the cone of the head that is active during the screwing in, does not cause an expansion of the material into the plastic region. This can be readily determined for the participating materials by the customary tension-expansion diagram, taking into account the screw head/screw hole geometry.

Then, if the expansion region surrounding the passage hole is designed in accordance with a preferred execution at least partially as a web or part of an annulus, this region can advantageously be shaped in such a manner that the expansion is concentrated here, so that the dimensioning can take place in a defined manner adapted to the cone of the screw head.

It is especially favorable if the web or annulus has a constant width followed on both sides by an area of the plate with increasing web width, which makes possible a further simplification in the determination of the geometric dimensioning necessary for the desired expansions.

A passage hole preferably comprises at least two regions with an essentially constant width followed on both sides by a region of the plate with an enlarged web width. Since the plate has an essentially constant thickness, the cross section therefore also remains the same on the whole essentially over the length of the web-like and partially annular region. This results on the one hand in an especially favorable shaping of the bone plate in which the regions intended to contact the bone can be dimensioned separately from the regions guiding the screw heads, so that an advantageous separation of functions is the result. Moreover, the expansion regions of a screw hole are distributed in a defined manner on two web regions that "divide" the expansion, so that the deformation of the bordering pressure region can remain limited. Therefore, on the other hand the pressure surfaces actively resting on the bone are maximized whereas the expansion regions primarily receive the expansion tensions acting tangentially as regards the screw head and are therefore loaded in a defined manner so that a plastic material deformation and in any case a breaking of the web on account of overloading are reliably avoided.

The plate is advantageously designed in such a manner that the pressure region forms a constriction opposite the region surrounding the screw hole and comprising the webs or annulus parts. Therefore, the webs or parts can be designed in such a manner that they have a maximum length as regards the regions acting as pressure surfaces, so that the relative expansion of the expansion regions is minimized. In this manner the requirement that the expansion zones extend beyond the elastic deformation region provided in the tension-expansion diagram can be met in an optimal manner.

The bone screw and/or the plate advantageously consist here of a titanium alloy compatible with the body. The tension-expansion diagram of the customary titanium alloys has an area of decreasing rise that merges via a plateau area into a falling course that characterizes the plastic behavior. According to a preferred embodiment, the expansion of the plate material necessary for the passage of the conical screw head in the region of the web or annulus area(s) surrounding the screw hole is selected in such a manner that an expansion area is selected in the curve in the upper area of the rise in which the transition to the horizontal begins in the peak region of the curve, whereas even the screw hole can generally have a taper that must only be dimensioned to be smaller in the screwing-in direction of the bone screw than the taper necessitated by the pitch of the cone of the screw head, in an optimally simplified embodiment only the screw head is conically tapered, whereas the fine thread of the screw hole is cylindrically constructed.

A further advantage is if the pitch of the fine thread is less on the screw head than the pitch of the thread on the shaft, which is active during the screwing into the bone. In this manner it can be achieved that when the screw head passes through the screw hole of the plate, the latter is drawn further to the bone by the screw head, so that the desired compression can be reliably achieved. This can be delicately adjusted by the fine thread in the plate and at the same time it is ensured that good antirotation is brought about by the tensile stress of the web-shaped material of the hole area surrounding the screw head, which protection extends over a rather long screw path. This is an advantageous contrast to the customary screw connections of the art, which merely require a rotation about an extremely slight angle of rotation in the tightened state in order to pass into the loose, readily rotatable state.

Moreover, the screw head can be lowered so low that it does not project above the plate surface. It therefore does not form any problematic hindrance as regards the snugness of the plate and in particular also cannot be perceived or felt in the implanted state. This is achieved in accordance with an advantageous further development in that the thread base of the thread of the screw is widened, especially conically, in the vicinity of the head, and essentially follows the thread base of the adjacent fine thread on the head. In this manner, when the screw is screwed in, in the head region a certain space for the fine thread is created in the bone so that the head is not limited by the bone surface in its movement during the screwing in. In this manner its height can be adjusted in such a manner that its covering surface terminates with the surface of the bone plate.

In addition, according to another advantageous further development, if the screw head has an internal hexagon.

BRIEF DESCRIPTION OF THE DRAWINGS

An embodiment is explained in detail in the following using the drawings.

DETAILED DESCRIPTION OF THE DRAWINGS

Figure 1:
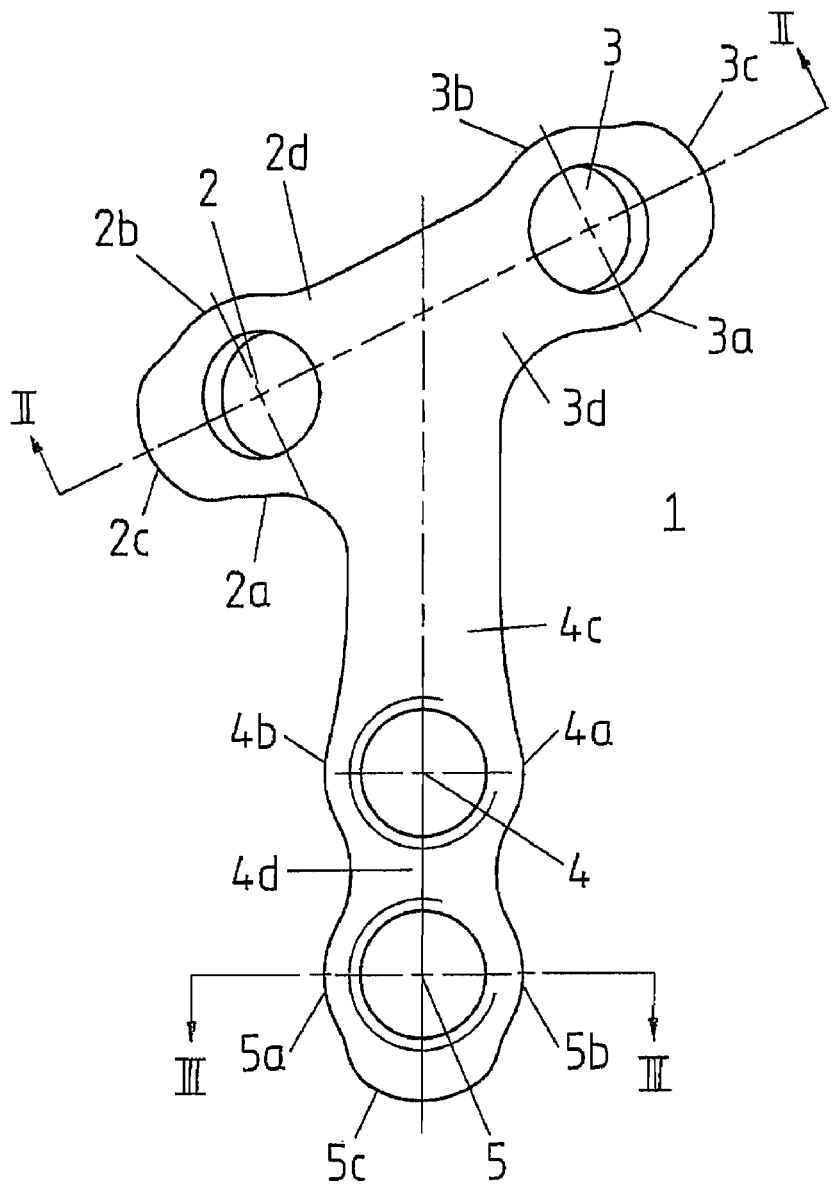
FIG. 1 shows the embodiment example of the bone plate in a top view.

In the embodiment example of FIG. 1, a bone plate 1 consisting of a titanium alloy compatible with the body is provided with passage openings 2 to 4 forming screw holes. Screw holes 2 to 4 are provided with a metric internal thread as is indicated by an annular line surrounding screw holes 2 to 5 (and further described in detail using the sectional images). The screw holes are partially surrounded by two web-shaped or partially annular regions 2a and 2b, 3a and 3b, 4a and 4b as well as 5a and 5b. These regions surrounding the particular passage hole are elastically constructed in such a manner that the material of the bone plate is not deformed into the plastic region by the expansion resulting as a consequence of the screwing in of the head of a bone screw, so that a stripping of the region surrounding the passage hole does not occur in any position of the bone screw by the interaction of the external thread of the head of the bone screw with the internal thread of the plate over the entire length of the thread while maintaining antirotation. These partially annular regions constructed as webs have a constant width viewed from the top. Since the plate thickness is also essentially constant, the webs have a cross section that remains essentially the same, which has the result that the differential expansions remain the same over the length of the web-shaped or partially annular region during the screwing in of the bone screw.

A zone 2c and 2d, 3c and 3d, 4c and 4d as well as 4d and 5c follows web-shaped or partially annular regions 2a and 2b, 3a and 3b, 4a and 4b as well as 5a and 5b on both sides, which zone forms a constricted region of the plate, and which zones form cross-sectional widenings as regards the web-shaped or partially annular regions 2a and 2b, 3a and 3b, 4a and 4b as well as 5a and 5b. Region 4d constitutes such a region both as regards bore 4 as well as bore 5 since it is adjacent to both.

Figure 2:
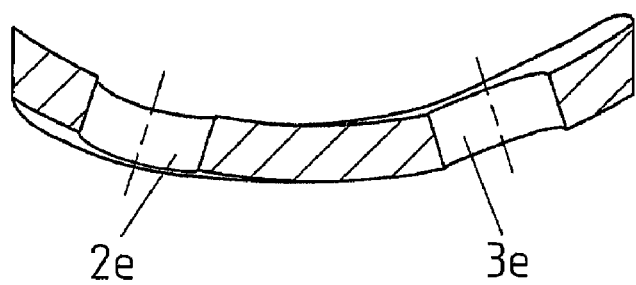
FIG. 2 shows a section through the embodiment example according to FIG. 1 along section line II in FIG. 1.

FIG. 2 shows a section of the plate according to sectional line II-II in FIG. 1.

Bores 2 and 3 with their threaded bores 2e and 3e are shown. It is apparent that plate 1 has a curved profile, which curvature is selected in accordance with the bone surface. The threaded bores are therefore directed vertically to the bone surface.

Figure 3:
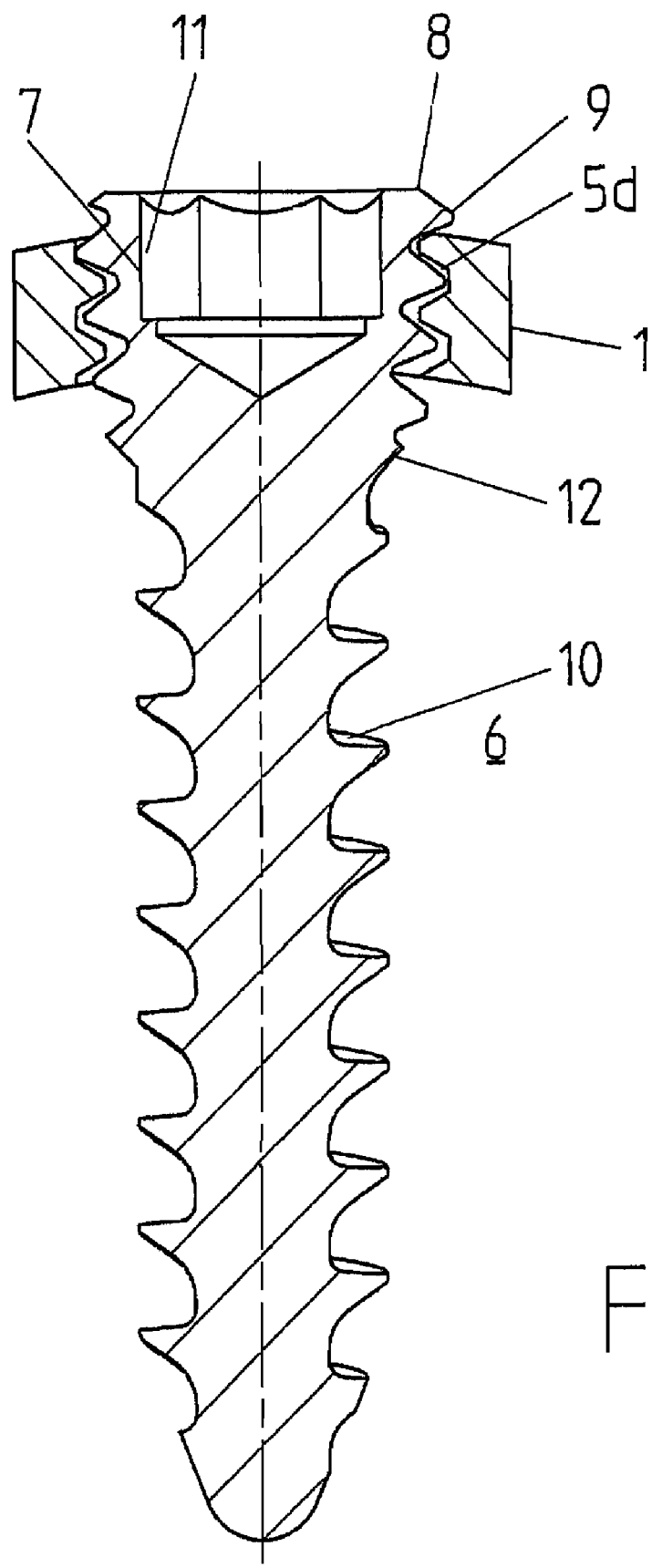
FIG. 3 shows another section through the embodiment example according to FIG. 1 along section line III in FIG. 1 with the bone screw, also shown in section, interacting with the bone plate shown.

FIG. 3 shows another section of the plate in accordance with sectional line III-III in FIG. 1. A bone screw 6 that also consists of titanium is inserted into threaded bore 5e of bore 5. It comprises a head 7 with an internal hexagon 11 provided with metric external thread 9 that widens out conically to the upper end 8, however, in contrast to the cylindrical internal thread 5d of threaded bore 5. Screw 6 has a bone screw thread 10 on the lower end whose pitch is greater than that of fine thread 9 on screw head 7.

It is apparent that, during the screwing in of bone screw 6, it penetrates at first by means of bone screw thread 10 into the bone and becomes fixed there until external thread 9 of head 7 engages into internal thread 5d of plate 1. Since the pitch of internal thread 5d is less than that of bone screw thread 10, with the further screwing in of screw 6 the plate begins to make contact with the adjacent bone during use. Since external thread 9 of head 7 widens upward, web areas 5a and 5b surrounding the latter (see FIG. 1) come under tension and begin to expand. The tensile stress that therefore builds up forms a protection for screw head 7 against unintended rotations. Since the region surrounding bore 5 forming the passage hole is elastically constructed in such a manner that the material of the bone plate is not deformed into the plastic region by the expansion resulting due to the screwing in of the head of the bone screw, a stripping of the webshaped or partially annular regions is avoided. This ensures that a stripping of the region surrounding passage hole 5 does not occur in any position of bone screw 6 by the interaction of external thread 9 of head 7 of bone screw 6 with the internal thread 5e of the plate over the entire length of the thread, while maintaining antirotation.

Screw 6 can now be screwed in so far that head 7 terminates flush with the surface of plate 1 in so far that it does not project above it in a problematic manner. Screw 6 can also be readily screwed entirely through plate 1 without it being permanently damaged. Thus, to this extent no stripping of the screw is even possible, which is usually associated in conventional screw connections with a destruction of the thread and with a formation of metal chips in the implantation area, which is absolutely to be avoided. Screw head 7 is sunk so deep here that it does not project above the plate surface. It therefore does not form any problematic hindrance as regards the snugness of the plate and in particular also cannot be perceived or felt in the implanted state. This is achieved in that the thread base of the thread of the screw is widened, especially conically, in a range 12 in the vicinity of the head, and essentially follows the thread base of the adjacent fine thread on the head. In this manner, when the screw is screwed in, in the head region a certain space for the fine thread is created in the bone so that the head is not limited by the bone surface in its movement during the screwing in. In this manner it can be adjusted in its height in such a manner that its covering surface terminates with the surface of the bone plate.

Screw 6 has an internal hexagon 11 in its head 7 for screwing in.

Figure 4:
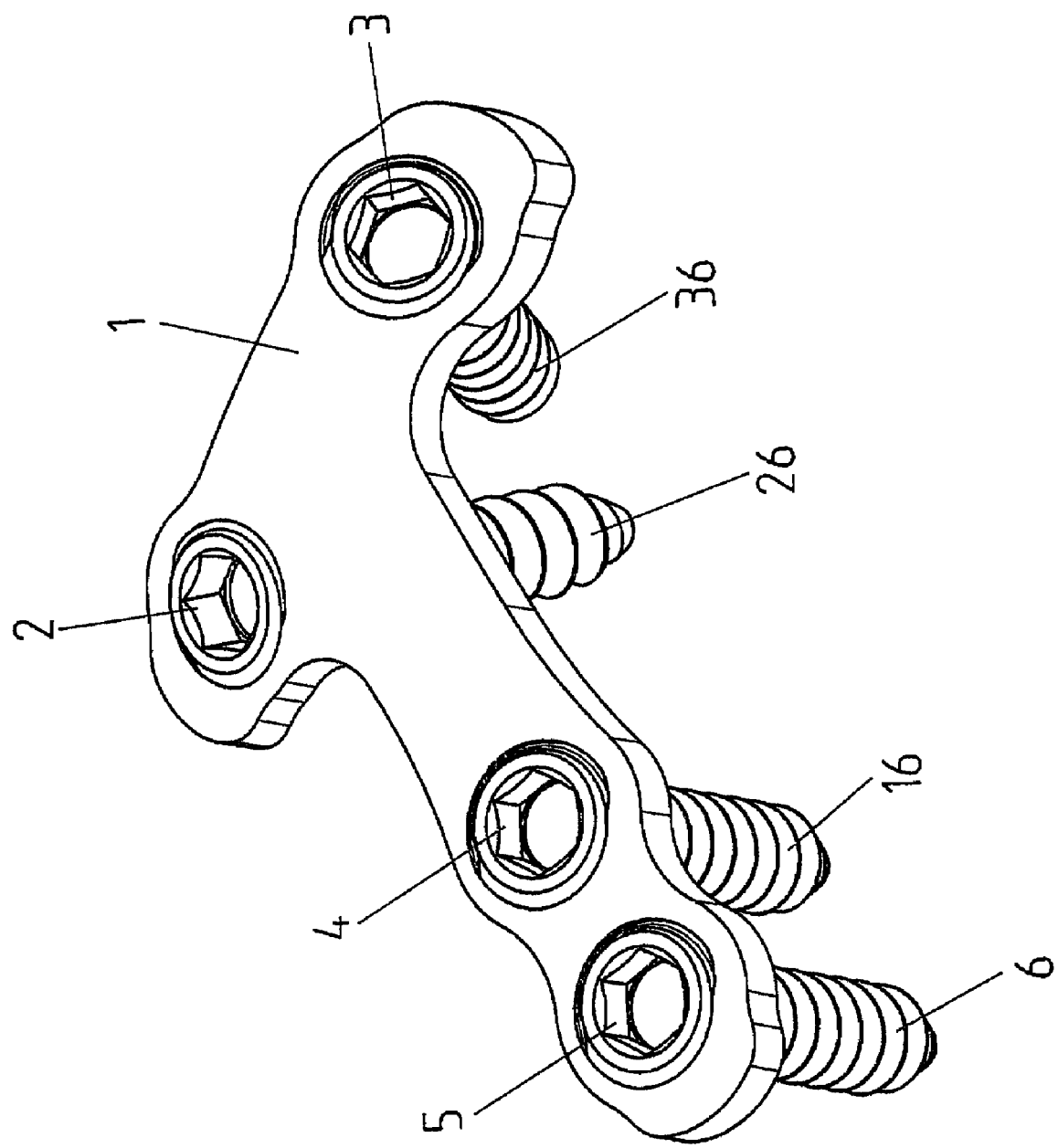
FIG. 4 shows a perspective view of the embodiment example of the plate with screwed-in screws in a perspective view.

FIG. 4 shows the complete bone plate 1 with screws 6, 16, 26 and 36 in a perspective view. It is apparent that the screws' directions are determined by the curvature of the surface of plate 1 and are stably guided by the internal thread of the holes interacting with the screw heads. The remaining elements can be identified by their reference numerals and are described above. Screws 6, 16, 26 and 36 are screwed so far into plate 1 in the direction given by the thread in the plate that even the thread engages the internal thread of the plate in the area of their heads. The screws can be adjusted here via their internal hexagons 2 to 4 in a broad range, during which the bone gripped by the thread of the screw is drawn toward the plate during the further screwing in of the screw if, according to the corresponding advantageous execution, the thread has a greater pitch on the shaft than the thread of the screw in its head area. An additional clamping of the screw occurs in the sense of antirotation if the internal and external threads of the screw deviate from one another in as far as they have a slight deviation in pitch or inclination. Inclination denotes here the shaping as cylindrical or conical thread with differing conicity.

The invention is not limited to the previously described embodiment example and can be used with numerous implants and bone plates when it is important to securely hold a bone screw on the one hand in different positions against unintended rotation and on the other hand to hold and position the screw head flush with the surface of the implant in such a manner that it does not project in a problematic manner.

What is claimed is:

1. A bone plate for attachment to a bone surface, the bone plate comprising:
   a plate comprising at least one screw hole defining a circular opening through the plate, each screw hole being at least partially surrounded by at least one elastically deformable portion of the plate; and
   a screw disposed in each screw hole, each screw having a conical head with an upper thread and a shaft with a lower thread, wherein the lower thread has a pitch that is greater than the upper thread;
   wherein the screw hole has a counterthread for engaging with the screw, and wherein the pitch of the upper thread is more severely tapered than the counterthread so that the head is securely clamped to the plate in an antirotational connection when the screw is screwed into the bone surface;
   wherein screwing the lower thread of the shaft into the bone surface causes the upper thread to engage the counterthread on the screw hole;
   wherein further screwing the lower thread of the shaft into the bone surface draws the head into the screw hole and widens the at least one elastically deformable portion of the plate without deforming remaining plastic portions of the plate, thereby forming tensile stress that clamps the screw to the plate and prevents unintended rotation of the screw;
   wherein further screwing the lower thread of the shaft into the bone surface increases the tensile stress in the plate around the at least one screw hole as the head is brought flush with the plate.

2. The bone plate according to claim 1, wherein further screwing of the lower thread of the shaft into the bone surface draws the head below an upper surface of the plate.

3. The bone plate according to claim 2, further comprising a base joining the upper and lower threads in a smooth conical transition.

4. The bone plate according to claim 3, wherein further screwing the screw into the bone surface causes the base to create space for the upper thread to engage with the bone surface.

5. The bone plate according to claim 1, wherein two separate elastically deformable portions at least partially surround the at least one screw hole and share the tensile stress.

6. The bone plate according to claim 5, wherein each screw hole is at least partially surrounded by constricted regions of the plate, and wherein the elastically deformable portions are formed such that the plastic regions of the plate are not deformed by expansion resulting as a consequence of the screw being screwed into the plate.

7. The bone plate according to claim 6, wherein the elastically deformable portions of the plate are formed such that stripping of the threaded screw hole does not occur when the screw is screwed entirely vertically though the plate.

8. The bone plate according to claim 1, wherein the elastically deformable portions of the plate are web-shaped.

9. The bone plate according to claim 1, wherein the elastically deformable portions of the plate are annular regions.

10. The bone plate according to claim 9, wherein the annular regions have a substantially constant width.

11. The bone plate according to claim 1, wherein the plate has a substantially constant thickness.

12. The bone plate according to claim 1, wherein the plate is made of titanium.

13. The bone plate according to claim 1, wherein the screw is made of titanium.

14. The bone plate according to claim 1, wherein the head has an internal hexagonal shape.

15. The bone plate according to claim 1, wherein the plate is curved.

* * * * *